United States Patent [19]

Nunokawa et al.

[11] Patent Number: 4,511,227

[45] Date of Patent: Apr. 16, 1985

[54] OPHTHALMIC APPARATUS HAVING MEANS FOR AUTOMATIC DETECTION OF APPROPRIATE POSITION OF EYE TO BE EXAMINED

[75] Inventors: Kazuo Nunokawa; Masayuki Masuyama, both of Tokyo, Japan

[73] Assignee: Tokyo Kogaku Kikai Kabushiki Kaisha, Tokyo, Japan

[21] Appl. No.: 304,575

[22] Filed: Sep. 22, 1981

[30] Foreign Application Priority Data

Sep. 24, 1980 [JP] Japan ................................. 55-132662

[51] Int. Cl.³ .......................... A61B 3/14; A61B 3/10; G03B 29/00
[52] U.S. Cl. ....................................... 351/208; 354/62
[58] Field of Search ........................... 351/208; 354/62

[56] References Cited

U.S. PATENT DOCUMENTS

| 4,187,014 | 2/1980 | Kato et al. | |
| 4,196,979 | 4/1980 | Kohayakawa et al. | 351/208 |
| 4,198,144 | 4/1980 | Matsumura et al. | 354/62 |
| 4,252,420 | 2/1981 | Kohayakawa | 351/208 |
| 4,257,687 | 3/1981 | Kohayakawa | 351/208 |
| 4,357,079 | 11/1982 | Karasawa | 351/208 |

Primary Examiner—Rodney B. Bovernick
Attorney, Agent, or Firm—Brumbaugh, Graves, Donohue & Raymond

[57] ABSTRACT

An ophthalmic apparatus having an automatic detection device of an appropriate position of the patient's eye. A target is projected through an aperture having two openings and through an objective lens to the patient's eye. The target projecting beam is reflected at the cornea of the eye and passed through the objective lens to form a target image. The position of the target image is detected photoelectrically by linear sensors or an area sensor.

3 Claims, 19 Drawing Figures

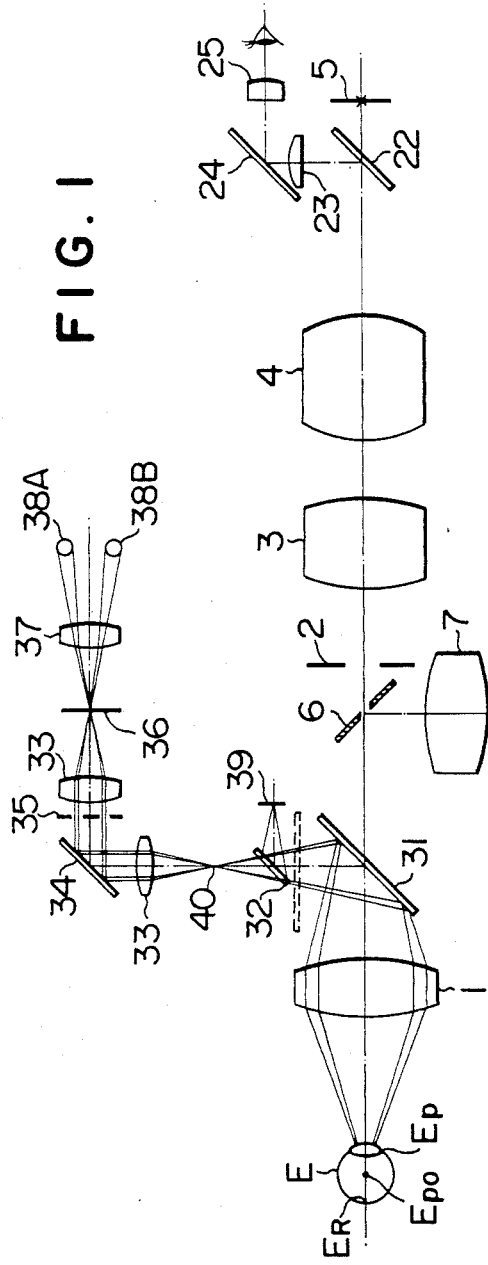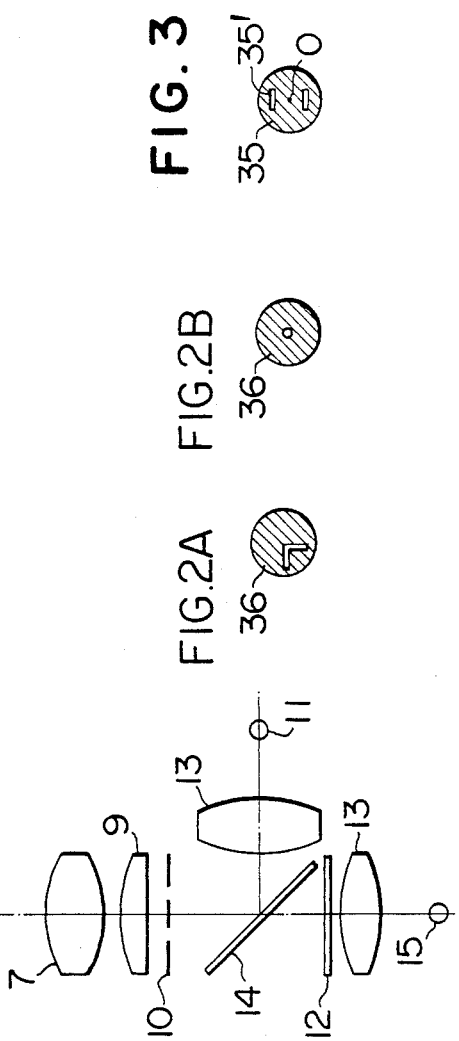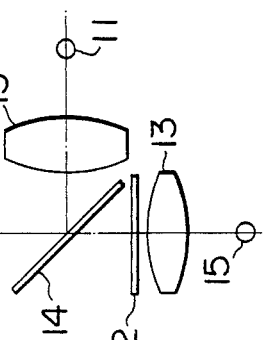
FIG. 1
FIG. 2A
FIG. 2B
FIG. 3

FIG. 4A
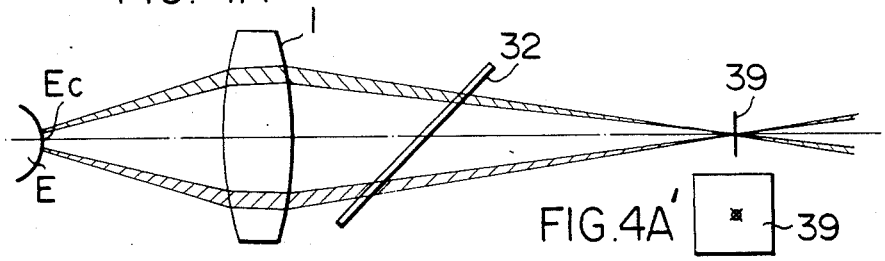
FIG. 4A'
FIG. 4B
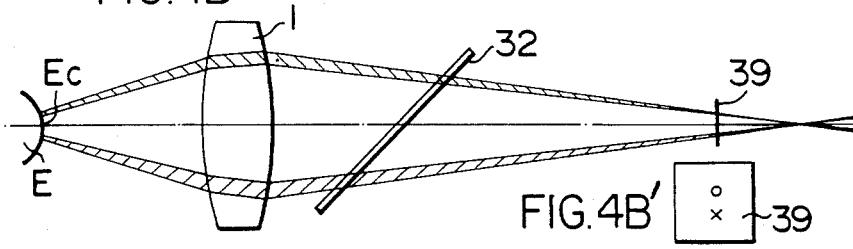
FIG. 4B'
FIG. 4C
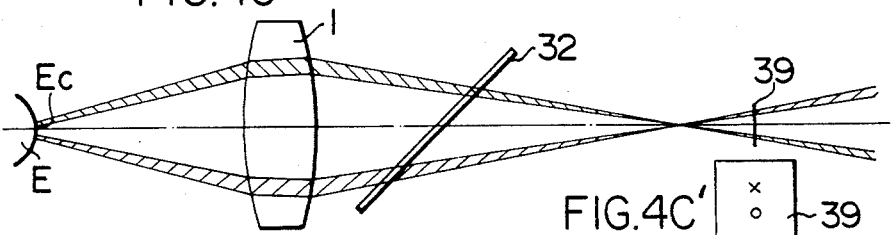
FIG. 4C'
FIG. 4D
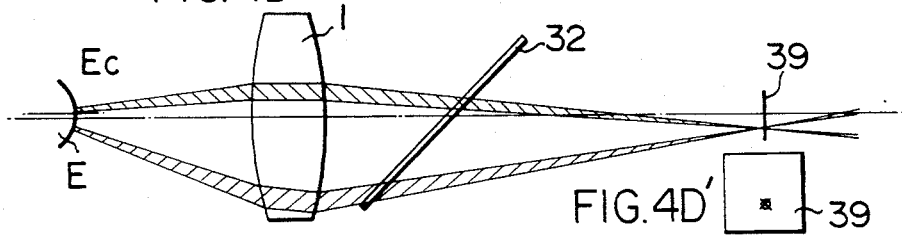
FIG. 4D'
FIG. 5
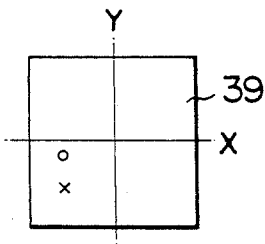
FIG. 6
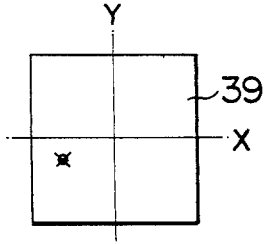

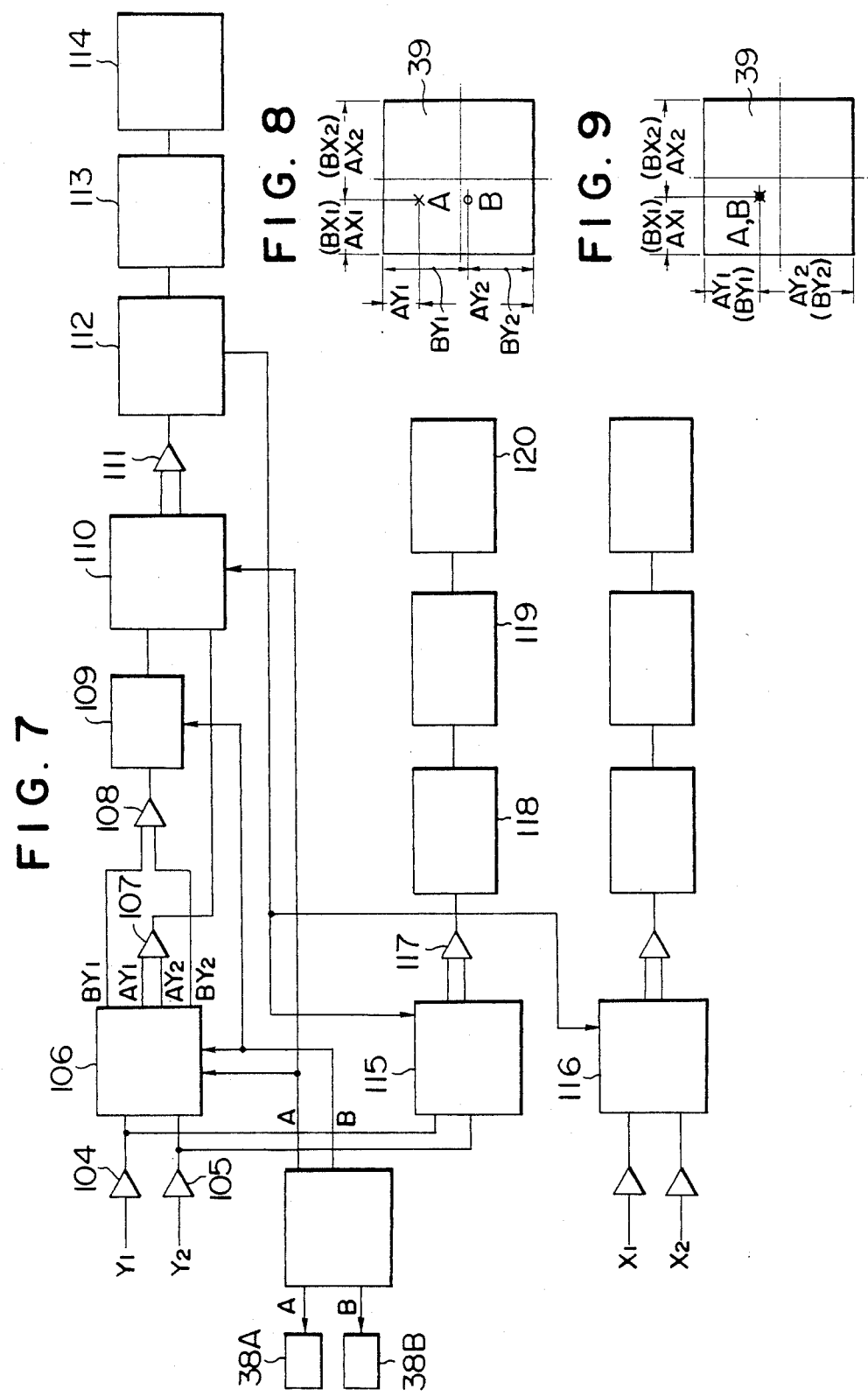

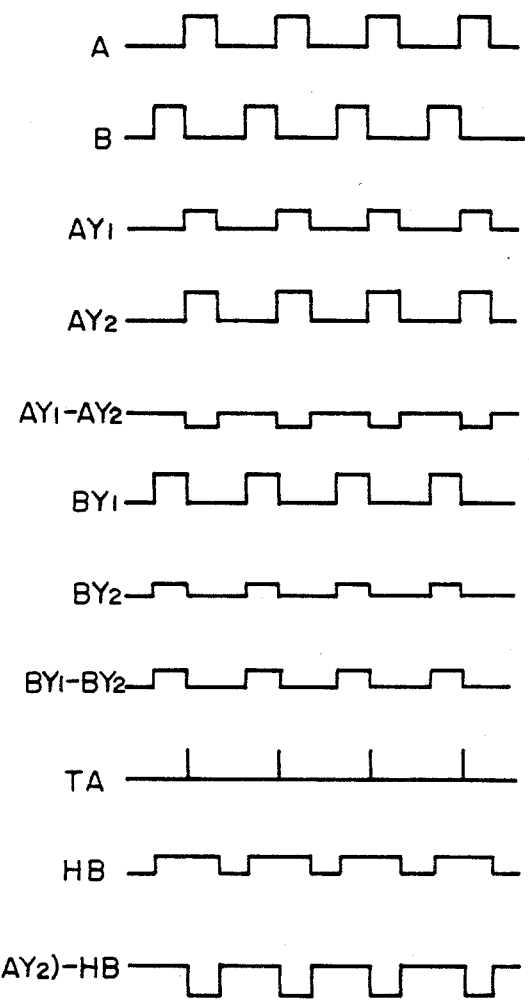

OPHTHALMIC APPARATUS HAVING MEANS FOR AUTOMATIC DETECTION OF APPROPRIATE POSITION OF EYE TO BE EXAMINED

The present invention relates to an ophthalmic apparatus, such as an ophthalmoscope, a funduscopic camera or a refractometer, provided with means for automatic detection of an appropriate position of an eye to be examined and constitutes an improvement over the ophthalmic instrument disclosed in my copending application, Ser. No. 473,454, filed Mar. 10, 1983.

An ophthalmic apparatus should be located at a position proper to an eye to be examined. Namely, aligning an ophthalmic apparatus with the optical axis of an eye to be examined (hereinafter referred to as "alignment adjustment") and maintaining an appropriate distance between the ophthalmic apparatus and the eye to be examined (hereinafter referred to as "working distance adjustment") are necessary. For example, in a funduscopic camera, if these adjustments are incomplete, beams of illuminating light reflected from the cornea are allowed to pass to a photographic optical path to cause a flare or ghost, and in a refractometer, if the working distance adjustment is incomplete, a measurement error is unavoidable. Various instruments have heretofore been proposed for detecting an appropriate position between an eye to be examined and an ophthalmic apparatus. However, these instruments are insufficient in various points when they are used for so-called automatic adjustment of automatically locating the ophthalmic apparatus at a position appropriate to an eye to be examined. For example, in order to enable the above automatic adjustment, the quantity of alignment adjustment and the quantity of working distance adjustment are independently detected photoelectrically and by utilizing the resulting detection signals, the ophthalmic apparatus should be moved three-dimensionally and furthermore, the ophthalmic apparatus should be shifted sequentially while following movements of the eye to be examined. In the conventional detection instrument, therefore, it is very difficult to obtain a high detection precision with a simple structure while satisfying the foregoing requirements. Therefore, various problems are left unsolved in utilizing such conventional detection instrument for automatic adjustment.

The present invention is to solve these problems involved in the conventional instruments and provide a detection instrument which automatically detects an appropriate positional relationship between an eye to be examined and an ophthalmic apparatus and enables independent and substantially simultaneous photoelectric detection of the quantity of alignment adjustment and the quantity of working distance adjustment. It is therefore a primary object of the present invention to provide an ophthalmic apparatus provided with a detecting instrument which can perform very easily so-called automatic adjustment of automatically controlling the ophthalmic apparatus to an appropriate position according to movements of an eye to be examined.

More specifically, in accordance with the present invention, there is provided an ophthalmic apparatus provided with means for automatic detection of an appropriate position of an eye to be examined, which comprises object lens means adapted to be positioned opposite to the eye to be examined with a working distance therebetween, target projecting optical system for projecting an image of target means to a cornea of the eye to be examined through said object lens means, said target projecting optical system including aperture means having at least two openings, photoelectrical means for detecting positions of target images produced by beams reflected at the cornea of the eye and passed through the objective lens means.

In the ophthalmic apparatus of the present invention, by adoption of the above-mentioned structure, an appropriate positional relationship between an eye to be examined and the ophthalmic apparatus can automatically be detected photoelectrically and three-dimensionally. Furthermore, changes of the appropriate positional relationship between the eye to be examined and the ophthalmic apparatus are sequentially followed by utilizing the resulting detection signals, whereby automatic adjustment can be performed very easily. Accordingly, the ophthalmic apparatus can be operated very easily by anyone and no particular skills are necessary for operation of the ophthalmic apparatus of the present invention.

The above and other objects and features of the present invention will become apparent from the following descriptions of a preferred embodiment taking reference to the accompanying drawings, in which;

FIG. 1 is an optical diagram illustrating an ophthalmic apparatus provided with means for automatic detection of an appropriate position of an eye to be examined;

FIG. 2A is a front view showing an example of the target;

FIG. 2B is a front view showing another example of the target.

FIG. 3 is a front view showing a two opening aperture;

FIGS. 4A–4D and 4A'–4D' are diagrams illustrating the principle of detection of an appropriate position of an eye to be examined;

FIGS. 5 and 6 are diagrams illustrating the states of formation of target images on a detector;

FIG. 7 is a diagram illustrating a circuit for detection of an appropriate position, alignment adjustment and working distance adjustment;

FIGS. 8 through 10 are diagrams illustrating the relation between a position of formation of target image and an electric signal; and, FIG. 11 is a diagram illustrating a wave form in the circuit shown in FIG. 7.

Referring to the drawings, particularly to FIG. 1, the photographic optical system comprises an object lens 1 adapted to be placed to be opposed to an eye E to be examined, an aperture 2 located in the vicinity of a position conjugate to the pupil Ep of the eye E to be examined with respect to the object lens 1, a focussing lens 3, an image forming lens 4 and a film 5. The finder optical system comprises a slanting reflecting mirror 22 disposed in front of the film 5, a field lens 23 located on a reflected beam path of the reflecting mirror 22, a reflecting mirror 24 and an eye lens 25.

The illuminating optical system comprises a slanting perforated mirror 6 inserted in an optical path of the photographic optical system in front of the aperture 2, a relay lens 7 disposed in a path of the beam reflected at the perforated mirror 6, a condenser lens 9, an annular slit 10, a flash tube 11 as the light source for photography, a heat-insulating filter 12, two condensing lenses 13, a half mirror 14 and an ordinary illumination light source 15. Illuminating beams from both the light sources are projected to the reflection face of the perforated mirror and reflected therefrom in the annular form and are passed to the fundus Er through the object lens 1 to illuminate the fundus Er.

The eye position detection optical system comprises a half-transparent mirror 31 slantingly disposed in the rear side of the object lens, which can be sprung up, a half-transparent mirror 32 disposed slantingly on an optical path for beams reflected from the reflecting mirror 31, a relay lens 33, a reflecting mirror 34, a two opening aperture 35, a target 36, a condenser lens 37, two light sources 38A and 38B disposed outside said optical path to turn on and off substantially alternately, and a photoelectric detector 39 disposed on the reflected beam optical path of the half-transparent mirror 32. Instead of the light sources 38A and 38B to be turned on and off alternately, there may be disposed a chopper for applying light to openings of the two opening aperture 35 alternately. At the time of observation or photographing, the half-transparent mirror 31 is sprung up and shifted to a position indicated by a dot line. The center Epo of the spherical face of the cornea of the eye to be examined, a point 40 for formation of an image of the target, the photoelectric detector 39 and the target are conjugate to one another, and furthermore, the object lens 1, the two opening aperture 35 and the light sources 38A and 38B are conjugate to one another. The photoelectric detector 39 consists of two linear sensors or area sensors traversing each other at a right angle. In the case where the linear sensors are used, the target 36 is of an L-figured opening as shown in FIG. 2A, and in the case where the area sensors are used, the target 36 is a pinhole as shown in FIG. 2B. The aperture 35 has two elongated openings 35' symmetric with each other with respect to the optical axis-passing point 0 as shown in FIG. 3.

The principle of detection of an appropriate position of the eye to be examined in the above-mentioned structure will now be described with reference to the case where the target 36 is a pinhole. FIG. 4A illustrates the case where the flux of the target projecting beams reflected from the cornea Ec of the eye E to be examined is focussed to form an image on the photoelectric detector 39 through the object lens 1 and the half-transparent mirror 32. An arrangement is made such that the light flux directed to the eye E by the object lens forms an image at the center of curvature of the eye E when the eye E is located at an appropriate position. In the case where the eye to be examined is located at an appropriate position, that is, both the alignment adjustment and working distance adjustment are complete, as shown in FIG. 4A, an image of the target is formed on the optical path of the photoelectric detector. More specifically, as shown in FIGS. 4A and 4A', the point x where the light flux from the light source 38A, which is hatched with lines falling down to the left, falls on the photoelectric detector 39 is in agreement with the point o where the light flux from the light source 38B, which is hatched with lines falling down to the right, falls on the photoelectric detector 39. In the case where the alignment adjustment is complete and the working distance is too short, as shown in FIG. 4B, the target image is formed in the rear of the photoelectric detector 39, and on the photoelectric detector 39, as shown in FIG. 4B', the points x and o are separate from each other symmetrically with the passing point of the optical path being as the center. In the case where the alignment adjustment is complete and the working distance is too long, as shown in FIG. 4C, the target image is formed in front of the photoelectric detector 39 and on the photoelectric detector 39, as shown in FIG. 4C', the points x and o are those opposite to the points x and o shown in FIG. 4B'. In the case where the working distance adjustment is complete and the alignment adjustment is incomplete, that is, the center of the spherical face of the cornea Ec of the eye to be examined is not present on the optical path of the object lens, as shown in FIG. 4D', the target images are formed at o the same position separate from the passing point of the optical path. In the case where both the working distance adjustment and the alignment adjustment are incomplete, the above-mentioned deviations appear on the photoelectric detector in combination.

Informations concerning the position of formation of the target image are converted to electric signals according to procedures described below, and the position of the ophthalmic apparatus relative to the eye to be examined is automatically detected based on these electric signals.

More specifically, when the light flux from the target arrives at the photoelectric detector 39, as shown in FIG. 5, it can be known from the information of the positional relationship between the points x and o in the direction Y, that is, the positional relationship in the vertical direction, whether the working distance is too short or too long, and the working distance is adjusted to produce the state shown in FIG. 6. An error of the alignment adjustment can be known from the information of the thus agreed points x and o in the directions X and Y, and the alignment adjustment is made based on this information.

Processing of the above-mentioned electric informations will now be described with reference to FIGS. 7 through 11. A synchronous signal generator 101 generates pulse signals A and B, and LED light sources 38A and 38B are alternately turned on and off by the pulse signals A and B. The beams from the LED light sources 38A and 38B are projected on the eye E to be examined by the eye position detecting optical system and are reflected on the cornea Ec of the eye E to be examined to form a target image on the photoelectric detector 39 as shown in FIGS. 8 through 10. The photoelectric detector 39 generates voltage signals $X_1$, $X_2$, $Y_1$ and $Y_2$ corresponding to co-ordinates $x_1$, $x_2$, $y_1$ and $y_2$ of the position of formation of the target image. The voltage signals $X_1$ and $X_2$ are voltage signals of the position of formation of the target image in the direction X, and the voltage signals $Y_1$ and $Y_2$ are voltage signals of the position of formation of the target image. When the target image is formed at the center of the photoelectric detector 39, $X_1$ is equal to $X_2$ and $Y_1$ is equal to $Y_2$ (see FIG. 10). Voltage signals corresponding to the position of the target image formed by beams from the LED light source 38A are represented by symbols $AX_1$, $AX_2$, $AY_1$ and $AY_2$, and voltage signals corresponding to the position of the target image formed by beams from the LED light source 38B are represented by symbols $BX_1$, $BX_2$, $BY_1$ and $BY_2$ (see FIG. 8). In order to adjust the working distance by using voltage signals in the direction so that $AY_1$ is equal to $BY_1$ and $AY_2$ is equal to $BY_2$ (see FIG. 9), the ophthalmic apparatus is moved relatively to the eye to be examined until the target images of beams from the light sources 38A and 38B are formed at the same position. The circuit for performing this adjustment will now be described. The voltage signals $Y_1$ and $Y_2$ from the photoelectric detector 39 are put in an analog switch 106 through amplifiers 104 and 105, and the analog switch 106 puts voltage signals $AY_1$ and $AY_2$ in a subtractor 107 and voltage signals $BY_1$ and $BY_2$ into a subtractor 108 according to signals A and B from the synchronous signal generator 101. The subtractors 107 and 108 put out signals $(AY_1-AY_2)$ and $(BY_1-BY_2)$, respectively. The signal from the subtractor 108 is applied to a holding circuit 109, and an electric signal HB held by a timing pulse signal synchronous with lighting of the light source 38B is put in an analog switch 110. The signal $(AY_1-AY_2)$ from the subtractor 107 and the signal A from the synchronous signal generator 101 are put in the analog switch 110, and the analog switch 110 performs a switching operation according to a timing pulse TA. The output from the analog switch 110 is put in a subtractor 111 which makes an operation of $[(AY_1-AY_2)-(BY_1-BY_2)]$. When the output of the subtractor 111 becomes 0, it is indicated that the position of the target image by beams from the light source 38A is in agreement with the position of the target image by beams from the light source 38B. The signal from the subtractor 111 is put in a direction discriminating circuit 112 to determine whether the control direction for adjustment is positive or negative. The signal from the direction discriminating circuit 112 is applied to a servo motor 114 through a motor driving circuit 113 to move the ophthalmic apparatus in the direction of the optical path of the object lens and effect control of the working distance. The above-mentioned control of the working distance is performed until the target images by beams from the light sources 38A and 38B become in agreement with each other and an appropriate working distance is obtained.

A circuit for the alignment adjustment by moving the ophthalmic apparatus in the vertical direction will now be described. Outputs $Y_1$ and $Y_2$ from the detector are put in an analog switch 115, and a signal from the direction discriminating circuit 112 is put in this analog switch 115 and this switch is put on when control of the working distance is completed. Since control of the working distance is completed when the alignment adjustment is started, two target images of beams from the light sources 38A and 38B are formed at the same position on the photoelectric detector, and it is not necessary to distinguish the positions of both the target images and it is sufficient if one of detection signals of the light sources 38A and 38B is used. In the present embodiment, signals $BY_1$ and $BY_2$ corresponding to the position of the target image of beams from the light source 38B are used. These signals $BY_1$ and $BY_2$ are put in a subtractor 117 and a signal $(BY_1-BY_2)$ put out from the subtractor 117 is put in a direction discriminating circuit 118 to determine whether the control direction is positive or negative. The signal from the direction discriminating circuit 118 is put in a servo system 120 through a motor driving circuit 119 to move the ophthalmic apparatus in the vertical direction and perform the alignment adjustment. The alignment adjustment in the horizontal direction is performed by using outputs $X_1$ and $X_2$ of the detector 39 in the same manner as described above with respect to the alignment adjustment in the vertical direction. Incidentally, if the working distance becomes improper while the above alignment adjustment is being conducted, the analog switches 115 and 116 are put off, and the alignment adjustment is stopped and the working distance adjustment is started again.

As will be apparent from the foregoing description, according to the present invention, the position of the ophthalmic apparatus can be detected three-dimensionally relatively to an eye to be examined by a simple structure by photoelectrically detecting the position of a target image. By utilizing electric signals generated by this photoelectric detection, the position of the ophthalmic apparatus can automatically be controlled and adjusted relatively to the eye to be examined.

The invention has thus been shown and described with reference to a specific embodiment, however, it should be noted that the invention is in no way limited to the details of the illustrated arrangements but changes and modifications may be made without departing from the scope of the appended claims.

We claim:

1. An opthalmoscopic apparatus comprising objective lens means having an optical axis and adapted to be positioned opposite to a patient's eye with a working distance, said patient's eye having a cornea with a center of curvature, means for detecting that the eye is properly positioned with respect to the objective lens means, said detecting means including a single target, a target image projection system adapted to project said target image by way of at least two light beams crossing each other on the optical axis of the objective lens means so that a target image is formed by each of the beams at the center of curvature of the cornea of the eye when the eye is properly positioned with respect to the objective lens means, a target image plane for forming target images, by mirror reflection at the cornea, of the light beams projected through the target projection system, whereby the spacing of the target images is changed in response to a change in the working distance and the target images are formed at the same position with the eye at the proper working distance.

2. An ophthalmoscopic apparatus in accordance with claim 1 in which said target includes two target elements which extend to intersect each other at a right angle, and said detecting means includes two linear sensors arranged to intersect each other at a right angle.

3. An opthamoscopic apparatus in accordance with claim 1 in which said target includes a point located on an optical axis of the apparatus and said detecting means includes an area sensor.

* * * * *